(12) United States Patent
Shrestha et al.

(10) Patent No.: US 9,471,747 B2
(45) Date of Patent: Oct. 18, 2016

(54) APPARATUS AND METHOD FOR VIEWING MEDICAL INFORMATION

(71) Applicant: UPMC, Pittsburgh, PA (US)

(72) Inventors: Rasu Bickram K. Shrestha, Allison Park, PA (US); Gonzalo Romero Lauro, Allison Park, PA (US); Harry Alton Black, Bridgeville, PA (US); Brian John Kolowitz, Pittsburgh, PA (US); Nathan John Lauffer, North Huntingdon, PA (US)

(73) Assignee: UPMC, Pittsburgh, PA (US)

( * ) Notice: Subject to any disclaimer, the term of this patent is extended or adjusted under 35 U.S.C. 154(b) by 138 days.

(21) Appl. No.: 13/733,326

(22) Filed: Jan. 3, 2013

(65) Prior Publication Data

US 2013/0179462 A1 Jul. 11, 2013

Related U.S. Application Data

(60) Provisional application No. 61/583,630, filed on Jan. 6, 2012.

(51) Int. Cl.
*G06F 7/00* (2006.01)
*G06F 17/30* (2006.01)
*G06F 19/00* (2011.01)

(52) U.S. Cl.
CPC ............. *G06F 19/30* (2013.01); *G06F 19/321* (2013.01)

(58) Field of Classification Search
CPC ........... G06F 17/30864; G06F 19/322; G06F 19/327; G06F 19/321; G06F 19/30; G06F 19/3406

USPC ............. 707/706, 769, 737, 722, 770; 705/2
See application file for complete search history.

(56) References Cited

U.S. PATENT DOCUMENTS

| | | | |
|---|---|---|---|
| 6,260,021 B1 | 7/2001 | Wong et al. | |
| 6,621,918 B1 | 9/2003 | Hu et al. | |
| 6,734,880 B2 | 5/2004 | Chang et al. | |
| 6,934,698 B2 | 8/2005 | Judd et al. | |
| 6,947,581 B1 | 9/2005 | Patel et al. | |
| 7,434,099 B2 * | 10/2008 | Flynn et al. | 714/26 |
| 7,505,614 B1 | 3/2009 | De La Torre-Bueno | |
| 7,523,505 B2 | 4/2009 | Menschik et al. | |
| 7,668,835 B2 | 2/2010 | Judd et al. | |
| 7,720,691 B2 | 5/2010 | Hasan et al. | |
| 7,778,851 B2 | 8/2010 | Schoenberg et al. | |
| 7,860,897 B2 | 12/2010 | Dettinger et al. | |
| 2002/0019751 A1 | 2/2002 | Rothschild et al. | |
| 2004/0034550 A1 | 2/2004 | Menschik et al. | |
| 2007/0022086 A1 | 1/2007 | Elscholz | |

(Continued)

FOREIGN PATENT DOCUMENTS

WO 2010070488 A1 6/2010

*Primary Examiner* — Md. I Uddin
(74) *Attorney, Agent, or Firm* — Tracey Belriger

(57) ABSTRACT

An apparatus includes a computer system programmed to retrieve information from a plurality of data sources; the computer system including a plurality of vault query services; an adapter for each of the data sources, each adapter translating an interface for one of the data sources to a vault query service interface; and a cross-vault query service providing an interface for data communication between an application program and the plurality of vault query services; and a user display for displaying the information retrieved from the data sources in response to a query from the application program.

18 Claims, 7 Drawing Sheets

(56) References Cited

U.S. PATENT DOCUMENTS

| | | |
|---|---|---|
| 2007/0203754 A1 | 8/2007 | Harrington et al. |
| 2008/0008401 A1 | 1/2008 | Zhu et al. |
| 2008/0103820 A1 | 5/2008 | Hasan et al. |
| 2008/0140723 A1 | 6/2008 | Hernandez et al. |
| 2008/0168107 A1 | 7/2008 | Parvatikar et al. |
| 2008/0208625 A1 | 8/2008 | Joseph |
| 2008/0221923 A1 | 9/2008 | Shogan |
| 2009/0080734 A1* | 3/2009 | Moriya et al. .................. 382/128 |
| 2009/0150176 A1 | 6/2009 | Gejdos et al. |
| 2009/0156906 A1 | 6/2009 | Liebman et al. |
| 2009/0265185 A1 | 10/2009 | Finn et al. |
| 2010/0076786 A1 | 3/2010 | Dalton et al. |
| 2010/0138231 A1* | 6/2010 | Linthicum et al. ................ 705/2 |
| 2010/0293164 A1 | 11/2010 | Weese et al. |
| 2011/0082859 A1* | 4/2011 | Deng ................. G06F 17/30451 707/728 |
| 2011/0145247 A1* | 6/2011 | Norris et al. .................. 707/737 |

* cited by examiner

FIG. 4

APPARATUS AND METHOD FOR VIEWING MEDICAL INFORMATION

CROSS-REFERENCE TO A RELATED APPLICATION

This application claims the benefit of U.S. Provisional Patent Application Ser. No. 61/583,630, filed Jan. 6, 2012, and titled "Apparatus And Method For Viewing Medical Information", which is hereby incorporated by reference.

BACKGROUND

1. Field of the Invention

Embodiments of the present invention relate to information systems, and more particularly to medical information systems.

2. Description of the Related Art

Medical images are commonly stored, distributed, and viewed in digital form using computer technology. Often however, electronic medical records regarding a specific individual may exist in many locations. Picture Archival and Communication Systems (PACS) and other imaging archives have been used to store medical images. In a typical PACS or other digital imaging archive and workflow application, image data obtained by imaging equipment such as CT (Computed Tomography) scanners, MRI (Magnetic Resonance Imaging) scanners, Whole Slide Imaging scanners, or other imaging sources are stored in the form of computer data files.

A large hospital system may be spread across a wide geographical area and may comprise numerous hospitals and imaging centers. These hospitals and imaging centers may have separate installations of PACS for Radiology and/or Cardiology and other distinct imaging archives for Anatomic Pathology, Oncology and other imaging specialties referred as "-ologies" that constitute distinct silos of information. The siloed and distributed nature of such disparate imaging systems may impede the efficiency of information retrieval for radiologists, cardiologists, pathologists or other diagnostic imaging specialists and referring clinicians alike.

Patients often get referred from one hospital to another for various reasons, but their imaging studies and reports may not be easily available, which may result in unnecessary repeat imaging studies, inferior imaging reports, and tedious searching of possible prior test results across multiple different PACS.

It would be desirable to provide a standards-based platform that links the PACS enterprise and all the other diagnostic imaging archives, and provides a unified view of all of a patient's prior tests and reports from across all hospitals and specialties in the system.

SUMMARY

In a first aspect, the invention provides an apparatus including a computer system programmed to retrieve information from a plurality of data sources; the computer system including a plurality of vault query services; an adapter for each of the data sources, each adapter translating an interface for one of the data sources to a vault query service interface; and a cross-vault query service providing an interface for data communication between an application program and the plurality of vault query services; and a user display for displaying the information retrieved from the data sources in response to a query from the application program.

In another aspect, the invention provides a method including: entering search criteria into a computer system programmed to retrieve information from a plurality of data sources; wherein the computer system includes a plurality of vault query services; an adapter for each of the data sources, each adapter translating an interface for one of the data sources to a vault query service interface; and a cross-vault query service providing an interface for data communication between an application program and the plurality of vault query services; and displaying the information retrieved from the data sources in response to the search criteria.

BRIEF DESCRIPTION OF THE DRAWINGS

FIGS. 4-7 are images of user interface displays.

DETAILED DESCRIPTION

In many cases, it would be useful to provide access to a comprehensive set of electronic medical records related to a given individual, including records that may be widely distributed across multiple entities. In one aspect of the invention, this can be accomplished with a system that retrieves information from multiple sources and presents that information on a user display in a manner that facilitates the use of the information by the user. This is referred to as the SingleView system.

The SingleView system can be implemented as a "federated system" with a "true imaging interoperability platform." The SingleView system departs from the previous siloed workflow (which separated radiology information systems (RIS), PACS and 3D imaging), to provide an integrated system. The SingleView system can display information in a manner that is patient-centric and workflow-based.

The SingleView system allows patient exams and records to be visually presented across multiple PACS, multiple imaging archives or other Information Systems, thereby preventing the repetition of patient records. This reduces the probability of unnecessary patient tests and suboptimal readings of patient reports. SingleView can alleviate these problems and improve workflow since physicians are spending less time per case.

Figure 1:
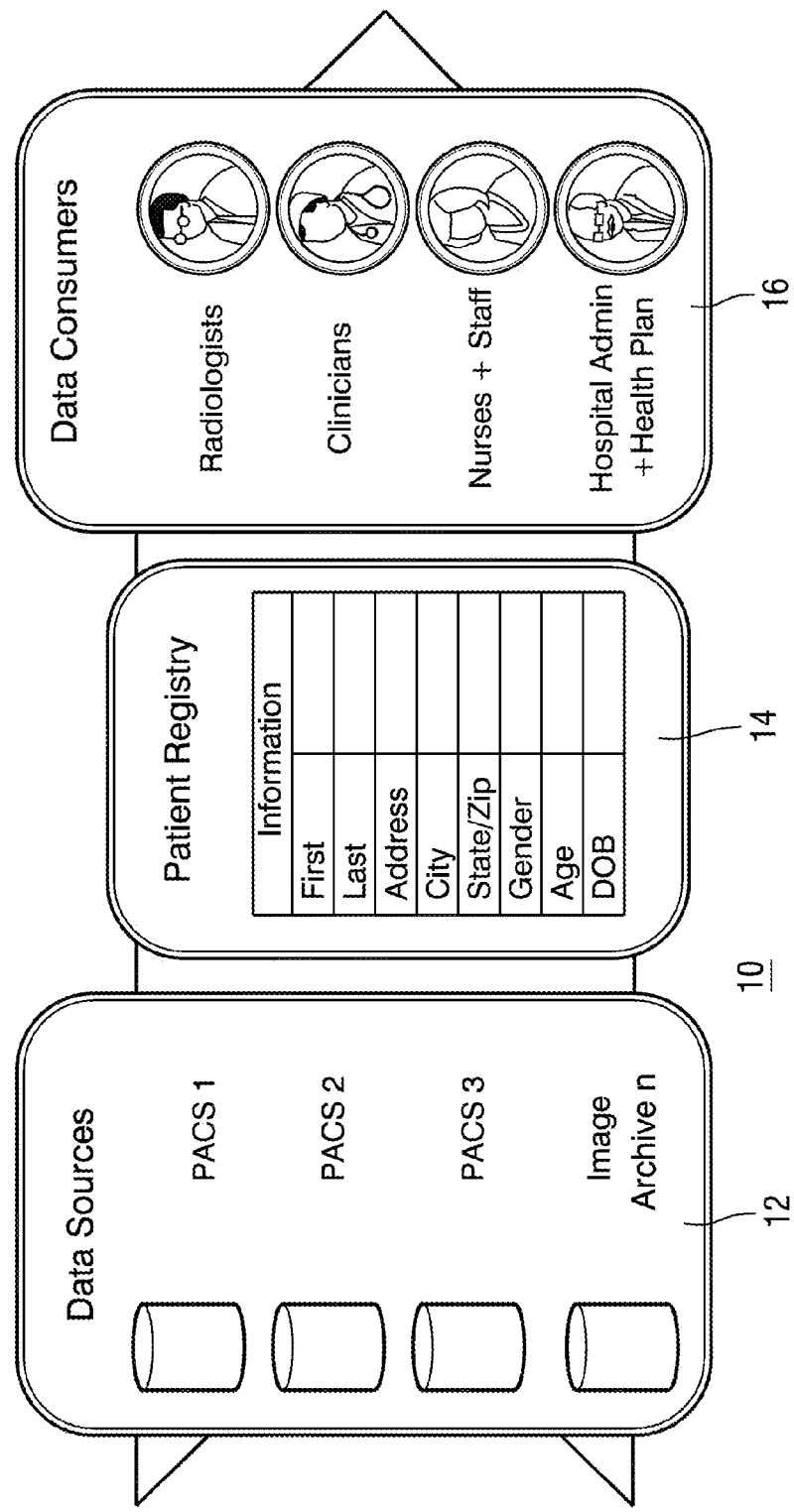
FIG. 1 is a schematic representation of medical data system.

FIG. 1 is a schematic representation of medical data system 10. The system includes a plurality of data sources 12, a patient registry 14 and a plurality of data consumers 16. The data consumers may include for example, radiologists, clinicians, nurses, staff, administrators and health plan personnel. The data consumers may wish to retrieve information from multiple PACS or other imaging archives. The patient registry includes patient information that can provide search criteria that is used to retrieve the information.

Figure 2:
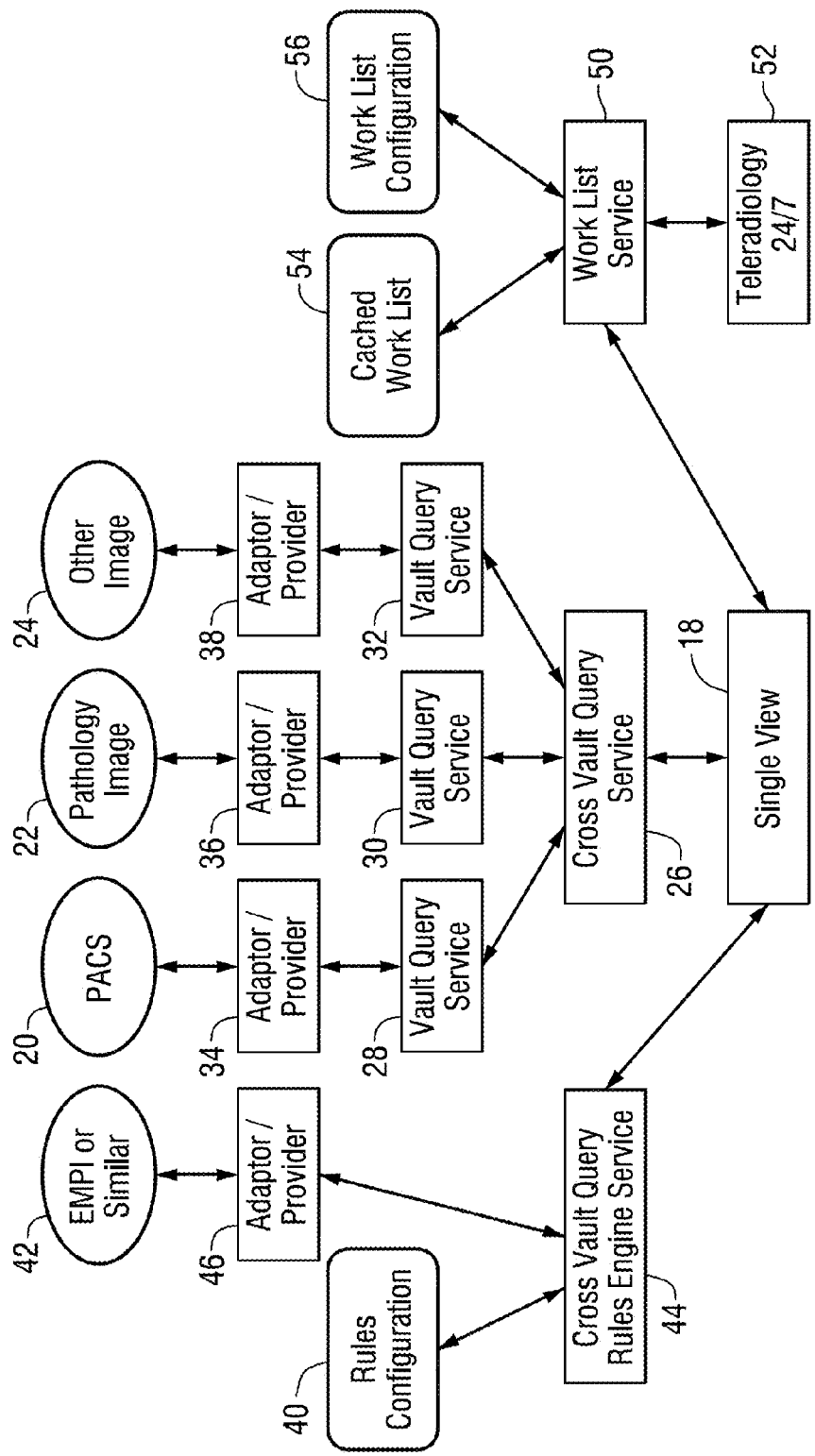
FIG. 2 is a functional block diagram of elements of a medical data system.

FIG. 2 is a functional block diagram of elements of a medical data system. The various elements of the system can be implemented using known computer or processing apparatus that is programmed to provide the functions illustrated in FIG. 2. The SingleView application program 18 interacts with other elements of the system to retrieve information from multiple imaging archives 20, 22 and 24. A cross-vault query service 26 provides an interface for data communication between the SingleView program and multiple Vault Query Services 28, 30 and 32. The cross-vault query service abstracts the complexity of querying multiple imaging archives from the calling applications. It allows the SingleView application program and any other client to treat the independent imaging archive silos as a single instance. The cross-vault query service takes the query, splits the request into N independent queries, asynchronously queries each PACS silo, and then combines the query responses and presents a single aggregated dataset to the calling application.

Adapter/Provider blocks 34, 36 and 38 provide a way to easily connect PACS to the Vault Query Service. The Vault Query service has a specific interface for communications with both the PACS and the Cross Vault Query Service. Each PACS or diagnostic imaging archive vendor may have a different query interface. The adapter translates the vendor specific interface into the Vault Query Service interface which allows the components to communicate. The provider aspect of the block adheres to a specific software engineering pattern that allows for the addition of new PACS or imaging archive Adapters to the system without modifying the Vault Query Service code.

The SingleView application program also interacts with a rules database 40 and an Enterprise Master Patient Index (EMPI) or similar database 42 through a cross-vault query rules engine 44. The EMPI service is an internal patient registry that links multiple patient instances together and identifies the instances though a single numeric identifier. An Adapter/Provider block 46 decouples the EMPI specific interface from the cross-vault query rules engine 44 as well as provides a standard way to plug-in new patient registry sources that provide similar functionality as EMPI 42.

The SingleView application also interacts with a user workstation 50 that is used to enter information requests and to display the requested information for the user. In the embodiment of FIG. 2, workstation can also interact with a teleradiology system 52, a cached worklist 54 and a worklist configuration 56. The teleradiology system 52 utilizes the SingleView framework to query the PACS silo's as a single PACS instance. This allows patients and exams from both internal and external PACS to be displayed on a single radiologist work list regardless of source PACS. The cached worklist 54 component allows for the storage of multiple consolidated views of the PACS silos. The worklist configuration 56 is an application that allows the user to build specific patient and exam queries for the teleradiology system 52 and cached worklist 54. This application allows the user to build query rules using a standard language and syntax otherwise known as the SingleView query language. The SingleView framework converts the SingleView query language into the PACS or other imaging archive specific syntax.

As shown in FIG. 2, the SingleView application can also serve as a platform for development of other imaging informatics related applications. It can, for example, be utilized for other previously developed applications such as 24/7 Teleradiology and an External Image Management System (EIMS).

Figure 3:
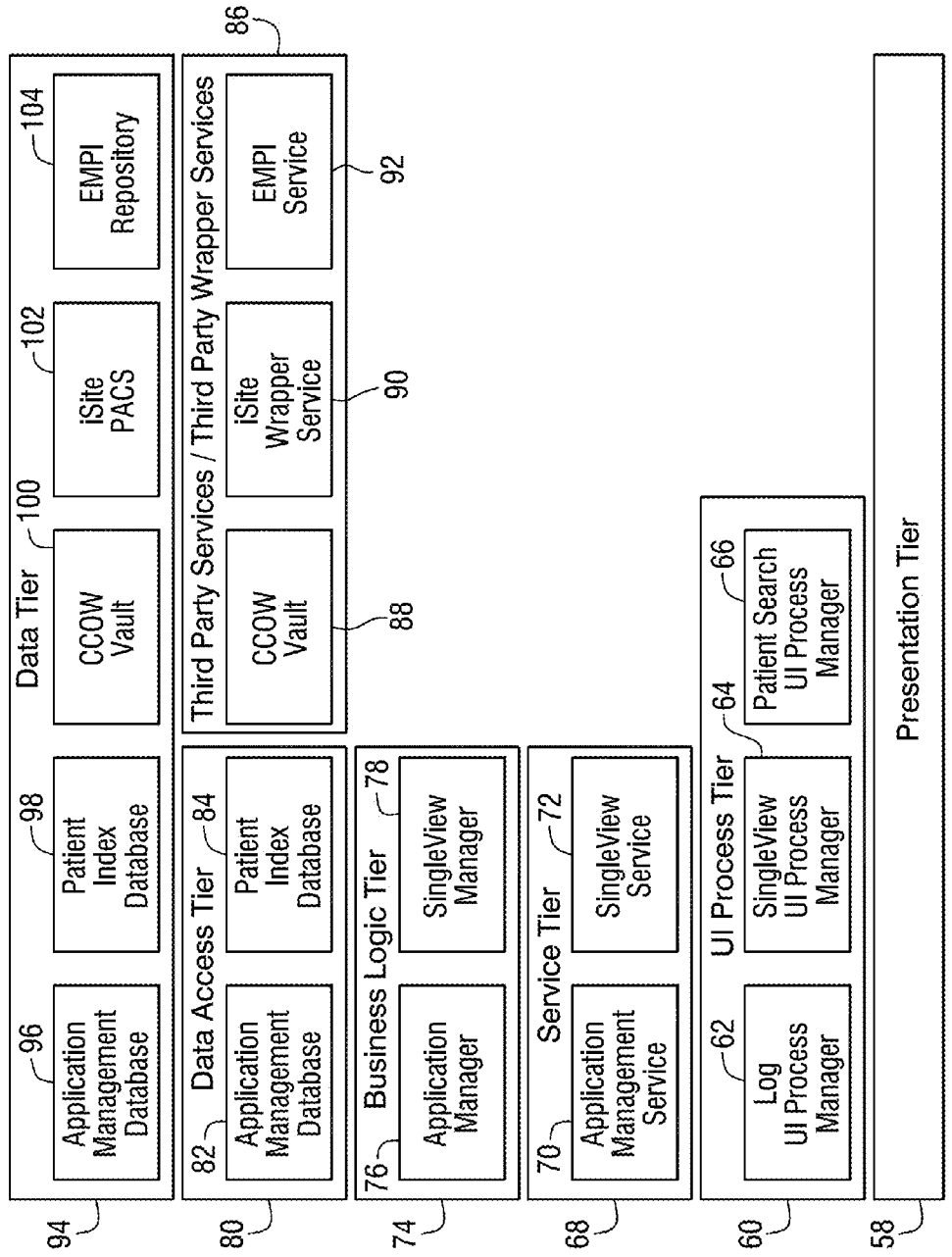
FIG. 3 is block diagram of software elements and a data structure of a medical data system.

FIG. 3 is block diagram of the software elements and data structure of a medical data system. These elements are illustrated as several tiers that can be implemented using computer hardware and software. The presentation tier 58 represents the display that shows the medical information to a user. The user interface (UI) process tier 60 includes a Log UI process manager 62, a User UI process manager 64, and a patient search UI process manager 66. These process managers can be implemented as software modules that perform the stated functions.

The service tier 68 includes an application management service 70 and a SingleView service 72.

The business logic tier 74 includes an application manager 76 and a SingleView manager 78.

The data access tier 80 includes an application manager 82 and a SingleView manager 84.

The third party service/third party wrapper service tier 86 includes Single Sign-On service 88, an iSite™ wrapper service 90, and an Enterprise Master Patient Index (EMPI) service 92. The Single Sign-On service provides the ability for applications to synchronize patient and exam context. Once the user is logged on to a workstation, the Single Sign-On service captures the user name and tracks which patient and exam the user is viewing for all Single Sign-On enabled applications. When the user loads a patient in one application, all other Single Sign-On enabled applications synchronize based on their patient or exam level integration.

The data tier 94 includes an application management database 96, a patient index database 98, a Single Sign-On vault 100, an iSite™ PACS 102, and an EMPI repository 104.

The SingleView framework is a unique approach to PACS and diagnostic imaging federation. Rather than attempting to create patient and exam registries, the SingleView framework relies on a business rule configuration to create Real-Time Virtual Patient Objects (RTVPO). Unlike patient and exam registries that require prepopulation of historical data and the registration of new data, the SingleView framework contains business rules. These rules are executed when the query is requested and direct the SingleView framework to query the appropriate data sources.

This rules-based framework provides a lightweight middleware layer that knows where to look for exams but is unaware of the existence of an exam. The rules-based approach of the SingleView framework allows for rapid integration or removal of data sources because historical data migration is not needed. The rules-based approach also allows for dynamic rules configuration to meet the organizational needs. Organizations can now agree to federate for a specific purpose or period of time without the need for a timely migration process. A research project that lasts only a few months or a Teleradiology agreement that operates only between the hours of 10 pm and 7 am are now candidates for federation.

The Real-Time Virtual Patient Object created by the SingleView framework can be used as a data source by other Information Systems. The SingleView Framework allows for the creation of endpoints such as IHE's XDS and XDS-I. The SingleView Framework contains service facades and adapters that simplify interfaces and adapt the interfaces in and out of the framework.

In operation, a user can submit a query from a workstation, and the system will retrieve relevant information based on the query and display the information on a display, that may be located at the workstation. The query may include patient information that will enable the system to find information relevant to a particular patient. Such patient information may include the patient name, patient ID number, social security number, birth date, etc.

Figure 4:
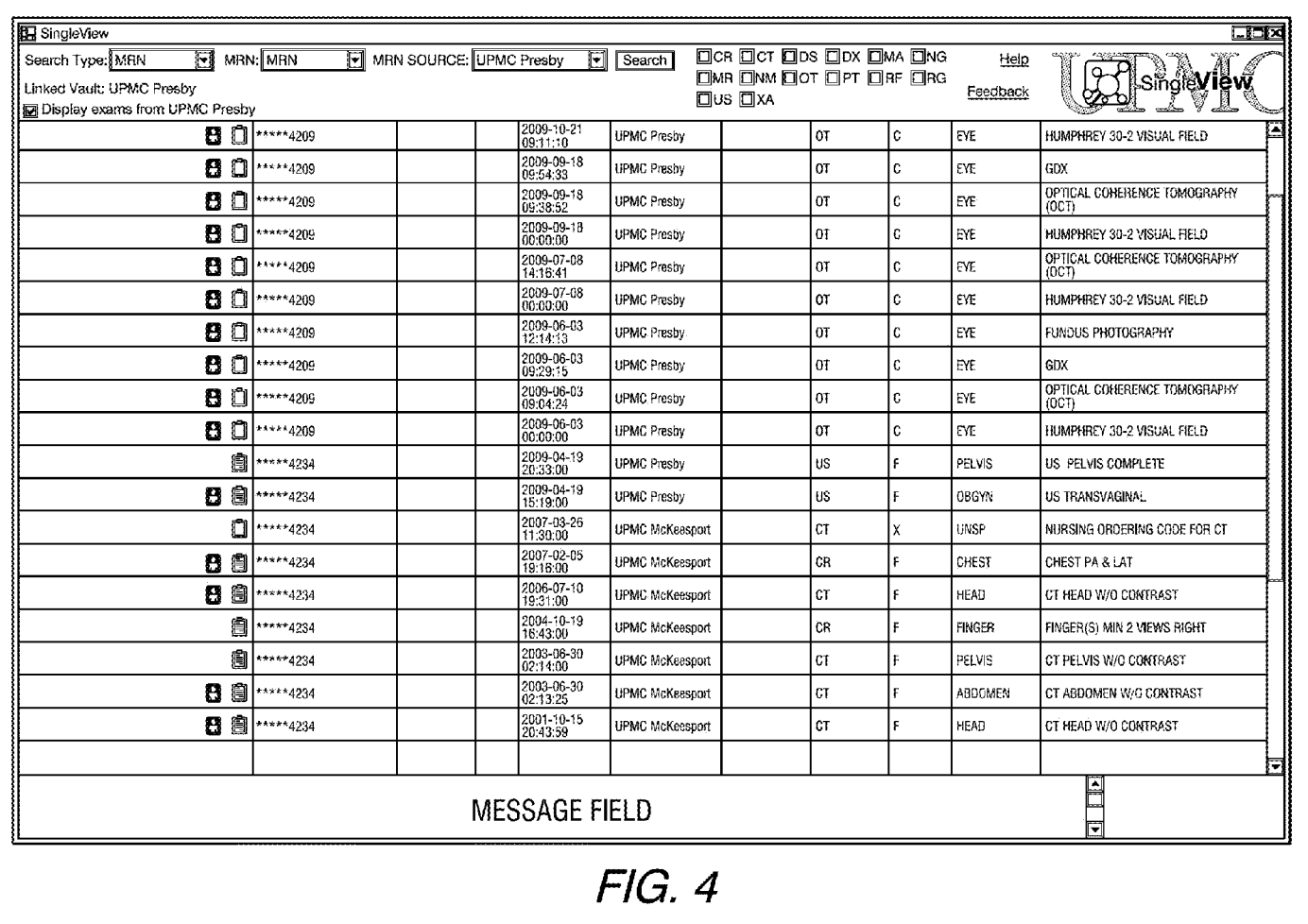

FIGS. 4-7 are examples of the type of information that may be retrieved and displayed on a user display. FIG. 4 shows a listing of events that have been retrieved based on a patient information query.

Figure 5:
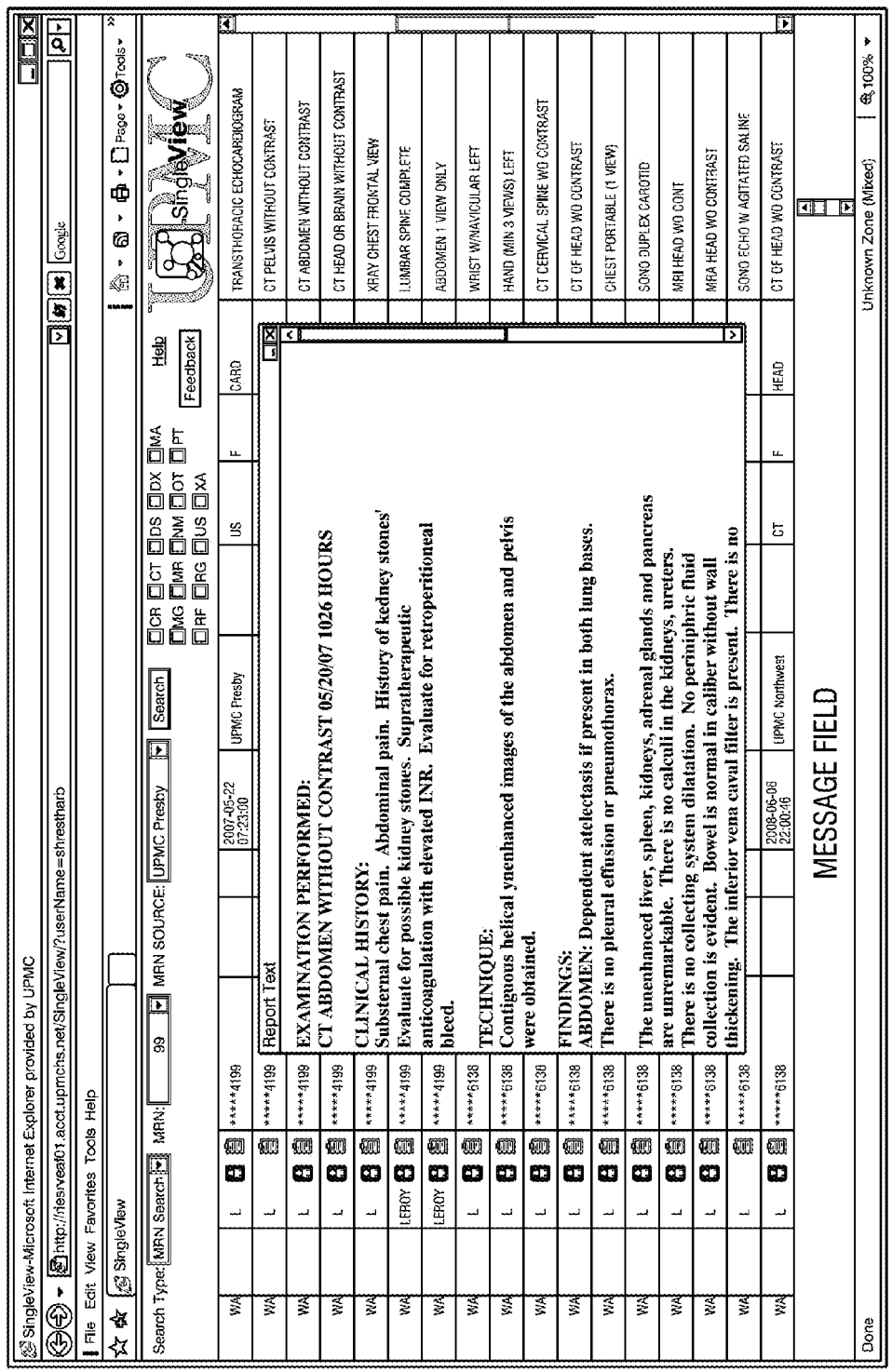

FIG. 5 shows a report text that can be retrieved by clicking on one of the events shown in the display of FIG. 4.

Figure 6:
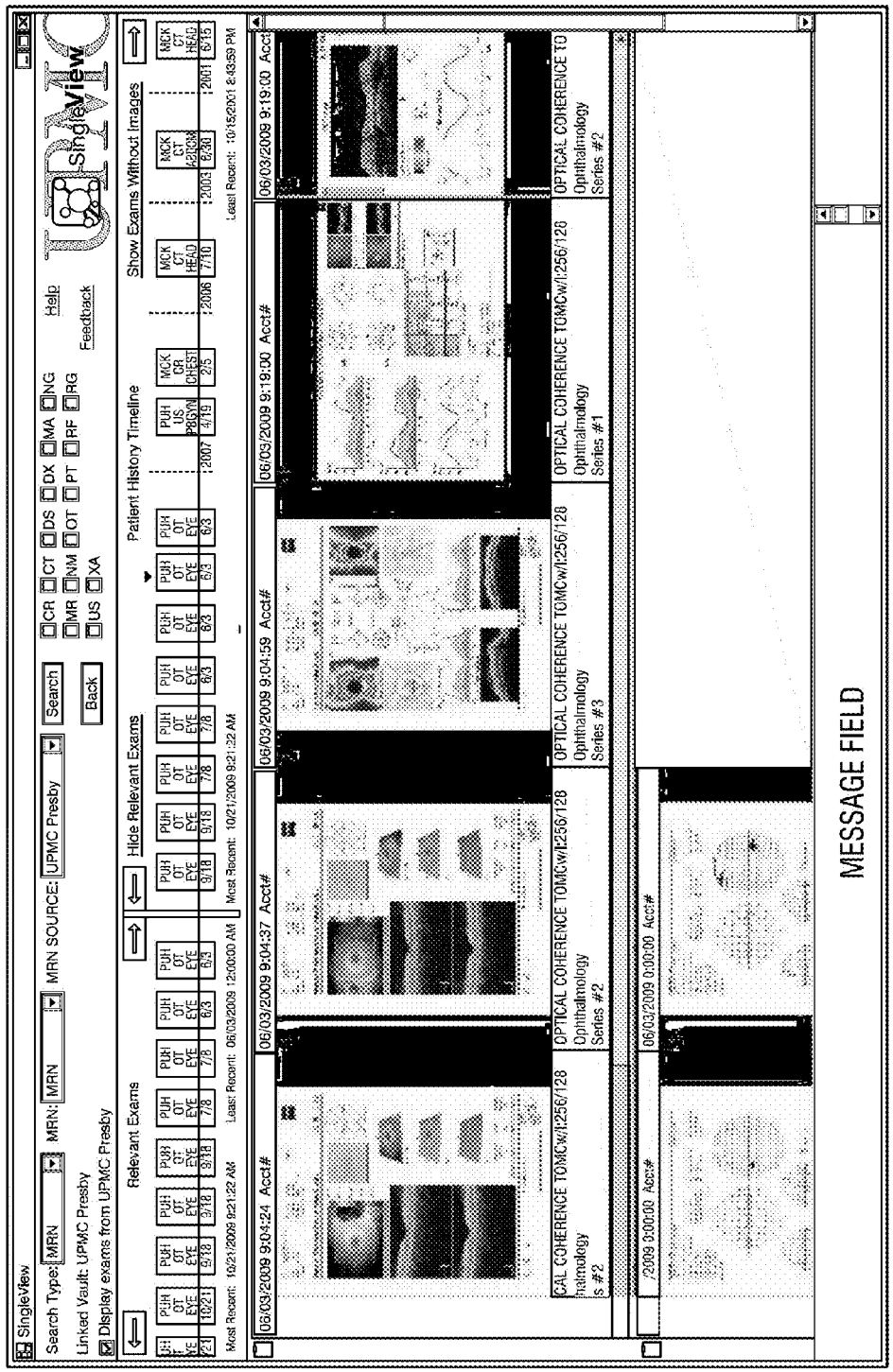

FIG. 6 shows a display having a plurality of images. A federated timeline is shown above the images. A plurality of icons or thumbnail images along the timeline shows various tests that have been performed and the relative timing of those tests. A user can click on these icons or thumbnail images to bring up larger images and other relevant information for the particular test. The federated timeline of the patient's studies visually presents the patient's exams across all instances of PACS or other diagnostic imaging archives in the federation.

Figure 7:
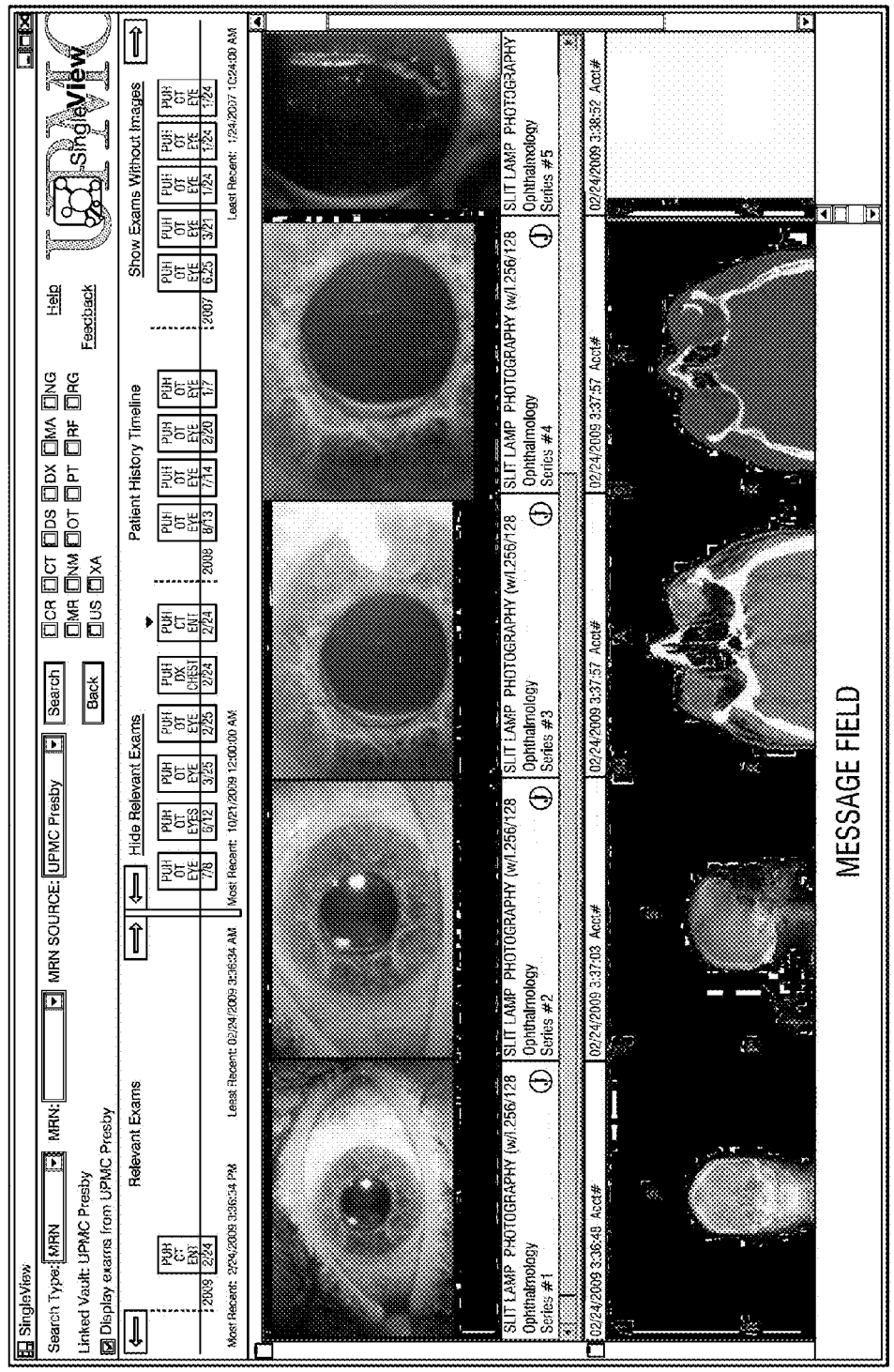

FIG. 7 is another display having a plurality of images and a timeline.

For the medical facility, the integration of the application may provide time efficiency, increased accuracy, and a decrease in the unnecessary repetition of scans and claim denials leading to facility-wide cost savings.

Embodiments of the invention organize relevant clinical information. SingleView essentially creates a 'Federated' PACS and diagnostic imaging archive, intelligently matching a patient's Medical Record Number (MRN) and other demographics with his/her other records across the enterprise and presents these in a single view. This imaging-centric platform can be integrated directly into a clinical workflow environment; providing a platform for imaging interoperability.

In various embodiments, a federation engine can be used to aggregate imaging data from across an organization's siloed imaging systems, including radiology PACS, Oncology PACS, Cardiology PACS, RIS, Cardio Vascular Information System (CVIS), Oncology Information Systems (OIS), Dermatology systems, Pathology systems, and others.

The described system can result in increased clinical efficiency; decreased time spent per case, and various facets of improved patient care. The system can also provide a robust functionality for identifying duplicate records within and across multiple systems and care venues, leveraging the Enterprise Master Patient Index (EMPI) web-services.

Conforming to the Integrating the Healthcare Enterprise (IHE) initiative. SingleView can be implemented using established standards-based architectures. SingleView leverages the PIX/PDQ (Patient Identifier Cross-referencing/Patient Demographic Query) components of the EMPI, and uniquely provides a workflow-centric imaging interoperability platform that is designed to be 'vendor-agnostic' and scalable.

SingleView has been designed to be standards based, and although it can leverage the API (Application Programming Interface) calls from various imaging vendors (for the visual controls), the application is not tied to one viewer and can be used even with open source viewing platforms.

Embodiments of the invention may be implemented, in part, using computer software applications executing on existing computer systems, e.g., desktop computers, server computers, laptop computers, tablet computers, and the like. The data communications techniques and distributed data nodes described herein, however, are not limited to any currently existing computing or data communications environment, and may be adapted to take advantage of new computing systems as they become available.

Further, embodiments of the invention (including the methods described herein) may be implemented as computer software applications and can be contained on a variety of computer-readable media. Illustrative non-transitory computer-readable media include, but are not limited to: (i) information permanently stored on non-writable storage media (e.g., read-only memory devices within a computer such as CD-ROM disks readable by a CD-ROM drive); and (ii) alterable information stored on writable storage media (e.g., floppy disks within a diskette drive or hard-disk drive). In other embodiments, the invention can utilize information conveyed to a computer by a communications medium, such as through a computer or telephone network, including wireless communications. The latter embodiment specifically includes information across the Internet and other data communications networks. Such computer-readable media and information conveyed on a communications medium, when carrying computer-readable instructions that direct the functions of the present invention, represent embodiments of the present invention.

In general, program routines created to implement an embodiment of the invention may be part of an operating system or a specific application, component, program, module, object, or sequence of executable instructions performed by a particular computing system. In addition, various computer software applications described hereinafter may be identified based upon the application for which they are implemented in a specific embodiment of the invention. However, it should be appreciated that any particular program nomenclature in the above description is used merely for convenience, and thus the invention is not limited to use solely in any specific application identified and/or implied by such nomenclature.

In one embodiment, the SingleView application can be developed on top of the SingleView Framework. The SingleView Framework is comprised of reusable components. This means that both extending SingleView and creating applications from the components that make up SingleView are quicker and more robust.

Each component of SingleView can be designed separately and an extensible architecture facilitates the "plug and play" addition and modification of these pieces. The platform can be provided with "out of the box" solutions for administrative tasks such as logging, monitoring, and configuration for all applications that use it.

In one implementation, an application architecture can include a .NET Framework 3.5 server-side platform, an ASP.NET 3.5 web platform, a C# server-side language; and XHTML, JavaScript, CSS and AJAX client-side technologies.

Conforming to the Integrating the Healthcare Enterprise (IHE) initiative, SingleView uses established standards-based architectures. SingleView leverages the PIX/PDQ (Patient Identifier Cross-referencing/Patient Demographic Query) components of the EMPI, and uniquely provides a workflow-centric imaging interoperability platform that is designed to be 'vendor-agnostic' and scalable.

The SingleView system has been designed to be standards-based, although it leverages the API (Application Programming Interface) calls from various PACS vendors (for the visual controls). In addition, it is not tied to one viewer and can be used even with open source viewing platforms.

By better acquiring, managing, and disseminating patient data, health care providers are able to free themselves from mundane data entry and data acquisition tasks. These tasks can consume time that could be otherwise allocated to providing care. The system can accommodate a growing diversity of modalities; a large span of medical disciplines; increased utilization of imaging annotations and feature extractions to support care and research; inclusion of images in regional, state, and national clinical data exchanges; and increased utilization of order entry and electronic medical record decision support algorithms to guide provider ordering behavior.

The examples presented herein are intended to illustrate potential and specific implementations of the present invention. It can be appreciated that the examples are intended primarily for purposes of illustration of the invention for those skilled in the art. No particular aspect or aspects of the examples are necessarily intended to limit the scope of the present invention.

It is to be understood that the figures and descriptions of the present invention have been simplified to illustrate elements that are relevant for a clear understanding of the present invention, while eliminating, for purposes of clarity, other elements. Those of ordinary skill in the art will recognize, however, that these sorts of focused discussions would not facilitate a better understanding of the present invention, and, therefore, a more detailed description of such elements is not provided herein.

In general, it will be apparent to one of ordinary skill in the art that some of the embodiments as described hereinabove may be implemented using software, firmware, and/or hardware. The software code or specialized control hardware used to implement some of the present embodiments is not limiting of the present invention. For example, the embodiments described hereinabove may be implemented in computer software using any suitable computer software language. Such software may be stored on any type of suitable non-transitory computer-readable medium or media such as, for example, a magnetic or optical storage medium. Thus, the operation and behavior of the embodiments are described without specific reference to the actual software code or specialized hardware components. It is understood that artisans of ordinary skill would be able to design software and control hardware to implement the embodiments of the present invention based on the description herein with only a reasonable effort and without undue experimentation.

In various embodiments of the present invention disclosed herein, a single component may be replaced by multiple components, and multiple components may be replaced by a single component, to perform a given function or functions. Except where such substitution would not be operative in practical embodiments of the present invention, such substitution is within the scope of the present invention. Any of the servers described herein, for example, may be replaced by a grouping of networked servers that are located and configured for cooperative functions.

While various embodiments of the invention have been described herein, it should be apparent, however, that various modifications, alterations and adaptations to those embodiments may occur to persons skilled in the art with the attainment of some or all of the advantages of the present invention. The disclosed embodiments are therefore intended to include all such modifications, alterations and adaptations without departing from the scope and spirit of the present invention as set forth in the appended claims.

What is claimed is:

1. An apparatus comprising:
    a computer system programmed to retrieve medical data related to an individual patient from a plurality of medical data sources;
    the computer system including a plurality of vault query services using a business rule configuration to create a real-time virtual patient object for the individual patient by a singleview framework wherein the singleview framework integrates or remove data sources without historical data migration;
    an adapter for each of the data sources, each adapter translating an interface for one of the data sources to a vault query service interface; and
    a cross-vault query service providing an interface for data communication between an application program and the plurality of vault query services; and using the real-time virtual patient object when a query is requested to query the data sources, wherein the cross-vault query service splits the query from the application program into N independent queries, asynchronously queries each of the medical data sources, combines medical data relating to the individual patient retrieved in response to the independent queries, wherein the application program interacts with an Enterprise Master Patient Index through a cross-vault query rules engine, and wherein the Enterprise Master Patient Index identifies multiple patient instances and presents a single aggregated dataset of the medical data for the individual patient to the application program; and
    a user display for displaying the medical data relating to the individual patient retrieved from the data sources in response to the query.

2. The apparatus of claim 1, wherein the application program uses patient information as search criteria that to retrieve the information.

3. The apparatus of claim 1, wherein the Enterprise Master Patient Index identifies multiple patient instances through a single numeric identifier.

4. The apparatus of claim 1, wherein the vault query service includes an interface for communications with both the data sources and the cross-vault query service.

5. The apparatus of claim 1, wherein the data sources comprise a plurality of imaging archives.

6. The apparatus of claim 1, wherein application program interacts with a workstation used to enter information requests.

7. The apparatus of claim 6, wherein the workstation uses worklists to assist a user in building specific queries using a standard language and syntax, and wherein the application program converts the a standard language and syntax into imaging archive specific syntax.

8. The apparatus of claim 1, wherein user display shows a timeline in combination with images retrieved from the data sources.

9. The apparatus of claim 8, wherein the images are shown as icons or thumbnail images.

10. A method comprising:
    entering search criteria into a computer system programmed to retrieve medical data related to an individual patient from a plurality of medical data sources;
    wherein the computer system includes a plurality of vault query services using a business rule configuration to a create real-time virtual patient object for the individual patient by a singleview framework wherein the singleview framework integrates or remove data sources without historical data migration; an adapter for each of the data sources, each adapter translating an interface for one of the data sources to a vault query service interface; and a cross-vault query service providing an interface for data communication between an application program and the plurality of vault query services, wherein the cross-vault query service splits the query from the application program into N independent queries, asynchronously queries each of the data sources, combines information relating to the individual patient retrieved in response to the independent queries, wherein the application program interacts with an Enterprise Master Patient Index through a cross-vault query rules engine, and wherein the Enterprise Master Patient Index identifies multiple patient instances and presents a single aggregated dataset of the information to the application program; and using the real-time virtual patient objects when a query is requested to query the data sources; and displaying the medical data relating to the individual patient retrieved from the data sources in response to the search criteria.

11. The method of claim 10, wherein the search criteria comprises patient information.

12. The method of claim 10, wherein the Enterprise Master Patient Index identifies multiple patient instances through a single numeric identifier.

13. The method of claim 10, wherein the vault query service includes an interface for communications with both the data sources and the cross-vault query service.

14. The method of claim 10, wherein the data sources comprise a plurality of imaging archives.

15. The method of claim 10, wherein application program interacts with a workstation used to enter search criteria.

16. The method of claim 15, wherein the workstation uses worklists to assist a user in building specific queries using a standard language and syntax, and wherein the application program converts the a standard language and syntax into imaging archive specific syntax.

17. The method of claim 10, wherein user display shows a timeline in combination with images retrieved from the data sources.

18. The method of claim 17, wherein the images are shown as icons or thumbnail images.

* * * * *